United States Patent [19]

Boon et al.

[11] Patent Number: 5,544,650
[45] Date of Patent: Aug. 13, 1996

[54] AUTOMATED SPECIMEN CLASSIFICATION SYSTEM AND METHOD

[75] Inventors: Mathilde E. Boon; Lanbrecht P. Kok, both of Lieveren, Netherlands; Laurie J. Mango, Rooevelt Island, N.Y.; Akiva Rutenberg; Mark R. Rutenberg, both of Monsey, N.Y.

[73] Assignee: Neuromedical Systems, Inc., Suffern, N.Y.

[21] Appl. No.: 196,982

[22] Filed: Feb. 14, 1994

Related U.S. Application Data

[63] Continuation-in-part of Ser. No. 179,060, Apr. 8, 1988, Pat. No. 4,965,725, and Ser. No. 420,105, Oct. 11, 1989, Pat. No. 5,287,272, which is a continuation-in-part of Ser. No. 425, 665, Oct. 23, 1989, Pat. No. 4,983,984, which is a continuation-in-part of Ser. No. 502,611, Mar. 30, 1990, abandoned.

[51] Int. Cl.$^6$ .................................................. G06F 159/00
[52] U.S. Cl. .......................... 128/632; 128/637; 382/133
[58] Field of Search ........................ 364/413.01, 413.04, 364/413.08, 413.1; 382/6, 15, 36; 128/632, 637

[56] References Cited

U.S. PATENT DOCUMENTS

| | | |
|---|---|---|
| 3,315,229 | 4/1967 | Smithline . |
| 3,333,248 | 7/1967 | Greenburg et al. . |
| 3,699,336 | 10/1972 | Ehrlich et al. . |
| 3,770,349 | 11/1973 | Legorretta-Sanchez .................. 356/73 |
| 3,824,393 | 7/1974 | Brain . |
| 3,826,899 | 7/1974 | Erlich et al. ......................... 325/92 PC |
| 4,000,417 | 12/1976 | Adkisson et al. . |
| 4,045,655 | 8/1977 | Suzuki et al. . |
| 4,048,616 | 9/1977 | Hart et al. . |
| 4,122,518 | 10/1978 | Castleman et al. . |
| 4,129,854 | 12/1978 | Suzuki et al. . |
| 4,139,303 | 2/1979 | Carlson et al. . |
| 4,175,860 | 11/1979 | Bacus . |
| 4,213,036 | 7/1980 | Kopp et al. ......................... 235/92 PC |
| 4,307,376 | 12/1981 | Miller et al. ............................. 356/39 |
| 4,404,683 | 9/1983 | Kobayashi et al. ......................... 382/6 |
| 4,501,495 | 2/1985 | Faulkner et al. . |
| 4,513,438 | 4/1985 | Graham et al. ............................. 382/6 |
| 4,523,278 | 6/1985 | Reinhardt et al. . |
| 4,591,980 | 5/1986 | Huberman et al. . |
| 4,601,055 | 7/1986 | Kent . |
| 4,612,614 | 9/1986 | Diendoerfer et al. . |
| 4,700,298 | 10/1987 | Palcic et al. . |

(List continued on next page.)

FOREIGN PATENT DOCUMENTS

| | | |
|---|---|---|
| 5433555 | 12/1974 | Japan . |
| 2093586 | 2/1982 | United Kingdom . |

OTHER PUBLICATIONS

Ercal et al., "Neural Network Diagnosis of Malignant Melanoma From Color Images", *IEEE Transactions on Biomedical Engineering,* vol. 41, No. 9, pp. 837–845 (The IEEE Engineering in Medicine and Biology Society Sep. 1994).

Wachtel et al., "Automated Analysis of Rat Breast Tumors, Comparison of Four Methods", *Analytical and Quantative Cytology and Histology,* vol. 13, No. 1, pp. 69–73 (37th Annual Scientific Meeting of the (American Society of Cytology, Louisville, Kentucky, Nov. 7–12, 1989).

(List continued on next page.)

*Primary Examiner*—Gail O. Hayes
*Assistant Examiner*—Frantzy Poinvil
*Attorney, Agent, or Firm*—Renner, Otto, Boisselle & Sklar, PLL

[57] ABSTRACT

A semi-automated method of classifying a histological specimen for the presence of premalignant or malignant cells, including the steps of treating a specimen with an immunohistochemical marker to provide a visual indication of cell proliferation, ranking individual objects in the specimen in an order according to the likelihood that each object has attributes consistent with a premalignant or malignant cell or cell cluster, selecting for display a set of said objects according to said ranking, and displaying images of said selected objects to facilitate review by an operator.

23 Claims, 2 Drawing Sheets

U.S. PATENT DOCUMENTS

| | | |
|---|---|---|
| 4,705,630 | 11/1987 | Gordon et al. |
| 4,805,225 | 2/1989 | Clark |
| 4,807,979 | 2/1989 | Saccomanno et al. |
| 4,821,118 | 4/1989 | Lafreniere |
| 4,833,625 | 5/1989 | Fisher et al. |
| 4,839,807 | 6/1989 | Doi et al. .......................... 364/413.13 |
| 4,965,725 | 10/1990 | Rutenberg .......................... 364/413.1 |
| 5,235,522 | 8/1993 | Bacus .................................. 364/497 |
| 5,257,182 | 10/1993 | Luck et al. .......................... 364/413.1 |

OTHER PUBLICATIONS

Gavin et al., "Morphometric Differences Between Cytologically Benign and Malignant Serous Effusions" *The Journal of Clinical Cytology and Cytopathology*, vol. 32, No. 2, pp. 175–182, (The International Academy of Cytology, Mar.–Apr. 1988.

"Neopath AutoPap 300 designed to analyze Pap smears without cytologist", MDDI Reports Gray Sheet, Sep. 23, 1991.

Abmayr et al., "*Progress Report of the TUDAB Project for Automated Cancer Cell Detection*", The Journal of Histochemistry and Cytochemistry, vol. 27, No. 1, pp. 604–612 (The Histochemical Society, Inc. 1979).

Bacus et al., "*Optical Microscope System for Standardized Cell Measurements and Analyses*", Applied Optics, vol. 26, No. 16, pp. 3280–3293 (Optical Society of America 15 Aug. 1987).

Bartels et al., "*High Resolution Prescreening Systems for Cervical Cancer*", Proceedings of the International Conference on Automation of Uterine Cancer Cytology, pp. 144–184, (Tutorials of Cytology, Chicago, Illinois 1976).

Bartels et al., "*A Self–Learning Computer Program for Cell Recognition*", Acta Cytologica, The Journal of Clinical Cytology, vol. 14, No. 8, pp. 486–494 (The Williams & Wilkins Company, Baltimore, MD 21202, Sep.–Oct., 1970).

Bengtsson, "*The Measuring of Cell Features*", Analytical and Quantitative Cytology and Histology, vol. 9, No. 3, pp. 212–217 (The International Academy of Cytology Jun. 1987).

Dayhoff et al., "*Neural Networks for Medical Image Processing: A Study of Feature Identification*", pp. 271–275, (SCAMC, Inc. Nov. 1988).

Dytch et al., "*An Interactive Microcomputer–Based System for the Quantitative Analysis of Stratified Tissue Sections*", Analytical and Quantitative Cytology and Histology, vol. 9, No. 1, pp. 69–78 (The International Academy of Cytology Mar. 1987).

Erhardt et al., "*FAZYTAN–A System for Fast Automated Cell Segmentation, Cell Image Analysis and Feature Extraction Based on TV–Image Pickup and Parallel Processing*", Analytical and Quantitative Cytology, vol. 2, No. 1, pp. 25–40 (The International Academy of Cytology Mar.–Apr., 1980, presented at the 1979 International Conference on Pattern Recognition of Cell Images, Chicago, IL, May 21–23, 1979).

Green entitled "*Parallel Processing in a Pattern Recognition Based Image Processing System: The Abbott ADC–500™ Differential Counter*", IEEE Computer Society Conference on Pattern Recognition and Image Processing, pp. 492–498 (IEEE ©1978).

Green, "*A Practical Application of Computer Pattern Recognition Research: The Abbott ADC–500 Differential Classifier*", The Journal of Histochemistry and Cytochemistry, vol. 27, No. 1, pp. 160–173 (The Histochemistry Society, Inc. 1979).

Kasdan et al., "*High Performance Pathology Workstation Using an Automated Multispectral Microscope*", Applied Optics, vol. 26, No. 16, pp. 3294–3300, (Optical Society of America Aug. 15, 1987).

Lloyd et al., "*Multiprocessing Interval Processor for Automated Cytogenetics*", Applied Optics, vol. 26, No. 16, p. 3356 (Optical Society of America Aug. 15, 1987).

Meyer, "*Automatic Screening of Cytological Specimens*", Computer Vision, Graphics, and Image Processing 35, pp. 356–369 (Academic Press. Inc. 1986).

Peet et al., "*A Computer–Assisted Cell Identification System*", Analytical and Quantitative Cytology, vol. 6, No. 1, pp. 59–70 (The International Academy of Cytology Mar. 1984).

Pratt, "*Digital Image Processing*", pp. 486–497, 500–512, (Wiley–Interscience, 1978).

Abstracts from "*The Second International Conference on Artificial Intelligence Systems(Expert Systems)as Diagnostic Consultants for the Cytologic and Histologic Diagnosis of Cancer*", (The International Academy of Cytology, American Society of Cytology, The Tutorials of Cytology at the University of Chicago) (Held Mar. 13–15, 1988 at the Drake Hotel Chicago, Il)publication date unknown.

Pycock et al., *Use of the MAGISCAN Image Analyser in Automated Uterine Cancer Cytology*, Analytical and Quantitative Cytology, vol. 2, No. 3, pp. 195–202 (The International Academy of Cytology Sep. 1980).

Reinhardt et al., "*Structure Analysis and Classification of Cervical Cells Using a Processing System Based on TV*", Analytical and Quantitative Cytology, vol. 1, No. 2, pp. 143–150, (The International Academy of Cytology Jul.–Aug. 1979).

Swank et al., "*Optical Automation For Sputum Cytology*", Applied Optics, vol. 26, No. 16, pp. 3373–3378 (Optical Society of America 15 Aug. 1977).

Tanaka et al., "*Automated Cytologic Screening System (CYBEST Model 4): an Integrated Image Cytometry System*", Applied Optics, vol. 26, No. 16, pp. 3301–3307 (The Optical Society of America, 15 Aug. 1987).

Tanaka et al., "*Fundamental Study on An Automatic Cytoscreening System Utilizing The Pattern Recognition System, III, A New System of Automated Apparatus (CYBEST) Utilizing The Pattern Recognition Method*", Proceedings of the International Conference of Automation of Uterine Cancer Cytology, (Tutorials of Cytology 1976).

Tanaka et al., "*CYBEST Model 4 Automated Cytologic Screening System for Uterine Cancer Utilizing Image Analysis Processing*", Analytical and Quantitative Cytology, vol. 9, No. 5, pp. 449–454 (The International Academy of Cytology Oct. 1987).

Tucker, *Automatic Screening of Cervical Smears, Machine Perception of Patterns and Pictures*, pp. 88–96, (Proceedings of the Conference Organized by the Physics in Industry Subcommittee of the Institute of Physics in collaboration with The National Physical Laboratory and The Institution of Electrical Engineers held at The National Physical Laboratory, Teddington, Middlesex, 12–14 Apr. 1972).

Tucker, "An Image Analysis System for Cervical Cytology Automation Using Nuclear DNA Content", The Journal of Histochemistry and Cytochemistry, vol. 27, No. 1, pp. 613–620, (The Histochemistry Society, Inc. 1979).

Vrolijk et al., "LEYTAS: A System for the Processing of Microscopic Images", Analytical and Quantitative Cytology, vol. 2, No. 1, pp. 41–48 (The International Academy of Cytology Mar.–Apr. 1980).

Wied, "Notice of Submission of Proposal to Government Agency", under grant No. 5 R35 CA42517–03 entitled Computer-Based Expert System For Cervical Cytology (University of Chicago, Division of Biological Sciences, publication date unknown).

Wied et al., "Expert Systems as Classifiers in Diagnostic Cytopathology", IEEE/Ninth Annual Conference of the Engineering in Medicine and Biology Society, pp. 1915–1917 (IEEE 1987).

Oldham et al., "Neural Network Recognition of Hammographic Lesions", 73rd Scientific Assembly & Annual Meeting of Radiological Soc. of North America (1987).

Watanabe, "A Pap Smear Prescreening System: CYBEST", pp. 227–240 (No Date).

Rosenthal, "Critical Review of Potential of Neural Nets in Diagnostic Pathology" (Abstract) (No Date).

Fukushima, "Self-Organizing Neural Network Models for Visual Pattern", Acta Neurosurgical, Suppl. 41 pp. 51–67 (1987).

Pao, "Adaptive Pattern Recognition and Neural Networks", Addison-Wesley Publishing Company (1989).

Tanaka et al, "CYBEST Model 3 & Automated Cytologic Screening System for Uterine Cancer Utilizing Image Analysis Processing", Analytical & Quantitative Cytology, vol. 4 pp. 279–285 (Dec. 1982).

Ansim™ User's Manual, VRSN 2.02, Science App. International Corp. (SAIC) (No Date).

Fukushima, "Neural Network Model for Selective Attention in Visual Pattern Recognition and Associative Recall", Applied Optics, vol. 26, No. 23 (1987).

Hall et al, "Microcomputer-Based Image Processing Workstations for Cytology", Applied Optics, vol. 26, No. 16, pp. 3266–3269 (1987).

Tanaka et al, "Automated Cytologic Screen System", Automated Cytologic Screen System, pp. 224–285 (Dec. 1982).

Coleman et al., "Clinical Cytotechnology", Butterworth & Co., Ltd., Chapter 25 (1989).

Deindoerfer et al., "'Yellow Iris' Urinalysis Workstation", Clinical Chemistry, vol. 31, No. 9, pp. 1491–1499 (1985).

Dud et al., "Sample Preparation in Diagnostic Cytology: Present Stat", Diagnostics & Clinical Testing, vol. 28, No. 3, pp. 16–19 (1990).

Egbert et al., "Preprocessing of Biomedical Images for Neural Computer Analysis", IEEE International Conference on Neural Networks, San Diego, vol. 1, pp. 561–568 (1988).

Tien et al., "Automated Cervical Smear Classification", IEEE/Ninth Annual Conf. of Engineering in Medicine & Biology (1987).

Lippmann, "An Introduction to Computing With Neural Nets", IEEE ASSP. Magazine (1987).

Koss, "Diagnostic Cytology and its Histopathologic Bases", J. B. Lippincott Company, pp. 1152–1153 (1979).

Rumelhart et al, "Parallel Distributed Processing", Massachusetts Institute of Technology, vol. 1 (1986).

Dayhoff et al, "Segmentation of True Color Microscopic Images Using a Back Propogation Neural Network", Neural Networks, vol. 1, No. 1, Suppl., p. 169 (Abstract) (1988).

"New Riverside University Dictionary", Houghton Mifflin Co., p. 974 (1984).

Rabal et al., "Astigmatic Holographic Processor for Local Pattern Perceptrons", Optics Communications, vol. 65, No. 5, pp. 343–346 (Abstract Only Cited) (1988).

Minsky et al., "Perceptrons", Perceptrons (1988).

Vlad et al., "Hybrid Holographic–Digital Processing System Of Three-Dimensional Displacement Measurement", Proceedings of The SPIE—The International Soc. for Optical Eng., vol. 700, pp. 344–345 (1986).

Rennie, "Cancer Catcher: Neural Net Catches Errors that Slip Through Pap Tests", Scientific American (Page Unknown, Reprint) (1990).

Megla, "An Automatic White Blood Cell Analyzer", SID Journal, vol. 11, No. 5, pp. 20–22 (Sep.–Oct. 1974).

Imasato, et al, "CYBEST: Automated Pap Smear Prescreener", Toshiba Review (International Edition) No. 100, pp. 60–63 (1975).

Hall et al., "Biology of Disease: Applications of Quantitative Microscopy in Tumor Pathology" University of California Laboratory Investigation, vol. 53, No. 1 (1985).

Rosenthal, "Automation of Uterine Cervical Cytology: Accomplishments" Elsevier Science Publishers pp. 65–72 (1986).

Hecht-Nielsen, "Neurocomputing: Picking the Human Brain", IEEE Spectrum (1988).

Mizuno, "A Neural Network Model for Pattern Recognition", Proceedings of 3rd Intern'l Workshop on Parallel Processing By Cellular Automats & Arrays, Berlin, GDR, 9–11, pp. 234–241 (1986).

"ICN Catalog of Biomedicals", ICN Biomedicals Inc., pp. 724–727 (No Date).

Vlad Inspec Abstract, "Proceedings of the SPIE—The Int'l Soc. for Optical Eng.", vol. 700, pp. 344–351 (1986).

Borowitz, "Laboratory Diagnosis Of Human Cancer Using Monoclonal Antibodies", Monoclonal Antibodies In Clinical Diagnostic Medicine, pp. 107–109 (No Date).

Becton-Dickinson Brochure, "The CAS 200 Workstation", (No Date).

5,544,650

1

AUTOMATED SPECIMEN CLASSIFICATION SYSTEM AND METHOD

This application is a continuation-in-part of Ser. No. 179,060, filed Apr. 8, 1988, now U.S. Pat. No. 4,965,725 and U.S. patent application Ser. No. 07/420,105, filed Oct. 11, 1989, now U.S. Pat. No. 5,287,272 entitled Automated Cytological Specimen Classification system and method; which is a continuation-in-part of Ser. No. 07/425,665 filed Oct. 23 1989, now U.S. Pat. No. 4,988,984 entitled Semi-automated Cytological specimen Classification Method including Ranking of cells; which is a continuation-in-part of Ser. No. 07/502,611, filed Mar. 30, 1990 entitled Automated Cytological Specimen, now abandoned, the entire disclosures of which are hereby incorporated by reference.

TECHNICAL FIELD OF THE INVENTION

This invention relates generally to cell classification, particularly to histology, and, more particularly, to a semi-automated method and apparatus for quickly and accurately classifying cells in a histological specimen based on cellular morphology.

BACKGROUND OF THE INVENTION

In the medical industry there is often the need for an experienced laboratory technician to review a histological or cytological specimen of biological matter for the presence of cells of a certain cellular type. An example of this is the need to review a Pap smear slide for the presence of malignant or premalignant cells. A Pap smear often contains as many as 100,000 to 200,000 or more cells and other objects, each of which a technician must individually inspect in order to determine the possible presence of very few malignant or premalignant cells. Pap smear tests, as well as other tests requiring equally exhausting cell inspection techniques, have therefore suffered from a high false negative rate due to the tedium and fatigue imposed upon the technician.

Several thousand women die each year in the United States alone from cervical cancer; a cancer from which a woman theoretically has a high probability of survival if detected in its early in situ stages. If not detected early, however, the chances of survival may decrease. If a malignant cell in a Pap smear is missed, by the time the woman has another Pap smear performed the cancer may have advanced. Consequently, the importance of detecting the presence of only one or a few malignant or premalignant cells among the hundreds of thousands of cells in a smear cannot be overstated. Unfortunately, present manual screening methods are inaccurate. In fact, recently some laboratories have been found to have incorrectly classified as benign up to 30% of the specimens containing malignant or premalignant cells. Also unfortunate is that many prior attempts to automate the cell inspection or classification have been unsuccessful.

Predominately, these prior attempts at automation have relied on feature extraction, template matching and other statistical or algorithmic methods alone. These attempts have required expensive and time-consuming cell preparations to distribute the cells and other objects over a slide so that none of the cells or objects overlap. However, even then these attempts have been unsuccessful at accurately classifying specimens in a reasonable time frame.

Attempts at automating the classification of histological specimens have also encountered difficulties. Histological specimens are essentially preserved slices of biological matter, for example tumors, and as such include many complex arrangements and architectures of cells in often overlapping or partially overlapping arrangements. Further, the cell architectures typical of malignancies may be presented in various orientations due to the method of slicing. These complexities in the cell architectures and cell presentations have made histological specimens difficult to classify using conventional automated techniques.

Immunochemical markers or labels are often used in histology for identifying certain characteristics of a cell, for example, whether the cell is undergoing mitosis or expresses a certain cancer related antigen. However, many immunochemical markers, including monoclonal antibodies, while being specific to a certain antigen also label unintended cells since the antigen may be expressed by other cells, such as cells specific to certain areas of the body recovering from injury. Consequently, classification systems which depend solely on the detection of cells expressing a certain antigen tend to be inaccurate.

Difficulties at automating cytological and histological specimens have been overcome by combining an algorithmic or statistical primary classifier with a neural network based secondary classifier and a tertiary human classifier as disclosed in U.S. Pat. Nos. 4,965,725 and 5,257,182 and U.S. patent application Ser. Nos. 07/420,105, 07/425,665, 07/520,611 and 07/610,423 which are incorporated in their entireties by this reference. A commercially available semi-automated specimen screening system, which employs a primary algorithmic classifier and a neurocomputer based secondary classifier to reduce the number of cells in a specimen to those most needing review by a technician is produced by Neuromedical Systems, Inc.® of Suffern, N.Y. under trademark PAPNET™.

SUMMARY OF THE INVENTION

The present invention provides a method and apparatus for semi-automating a cell classification process using at least primary and secondary classifications followed by review by a skilled technician. Specifically, the process analyzes a histological specimen and provides two summary screens of output images of the cells and cell clusters most likely to represent premalignant or malignant cells or cell clusters. In some embodiments the histological specimen may been stained, such as with an immunochemical maker which indicates cell proliferation or other cell activity. With the aid of a computer and mouse the technician can compute various diagnostically significant information in the displays.

In accordance with an aspect of the invention, a semi-automated method of classifying a histological specimen for the presence of premalignant or malignant cells, includes the steps of treating a specimen with an immunochemical marker to provide a visual indication of cell proliferation, ranking individual objects in the specimen in an order according to the likelihood that each object has attributes consistent with a premalignant or malignant cell or cell cluster, selecting for display a set of said objects according to said ranking, and displaying images of said selected objects to facilitate review by an operator.

Preferably, the invention includes the step of permitting the operator to edit the display to designate cells within the images of selected objects as proliferating or non-proliferating. The invention may also include the steps of counting certain designated cells as well as calculating the area of stained nuclei within the display.

In accordance with another aspect of the invention, a semi-automated method of classifying a histological specimen includes the steps of obtaining a histological specimen, classifying such specimen to determine the likelihood that individual objects in such specimen have attributes justifying further medical consideration, the classifying step including ranking individual objects in the specimen in an order according to the likelihood that each object has attributes justifying further medical consideration is justified, and selecting for display a plurality of such objects according to the order, said plurality of selected objects being less than the number of ranked objects and displaying an image of each of the selected objects for review and further classification by an operator.

These and other objects, advantages, features and aspects of the present invention will become apparent as the following description proceeds.

To the accomplishments of the foregoing and related ends, the invention, then comprises the features hereinafter fully described in the specification and particularly pointed out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

DETAILED DESCRIPTION OF THE INVENTION

Figure 1:
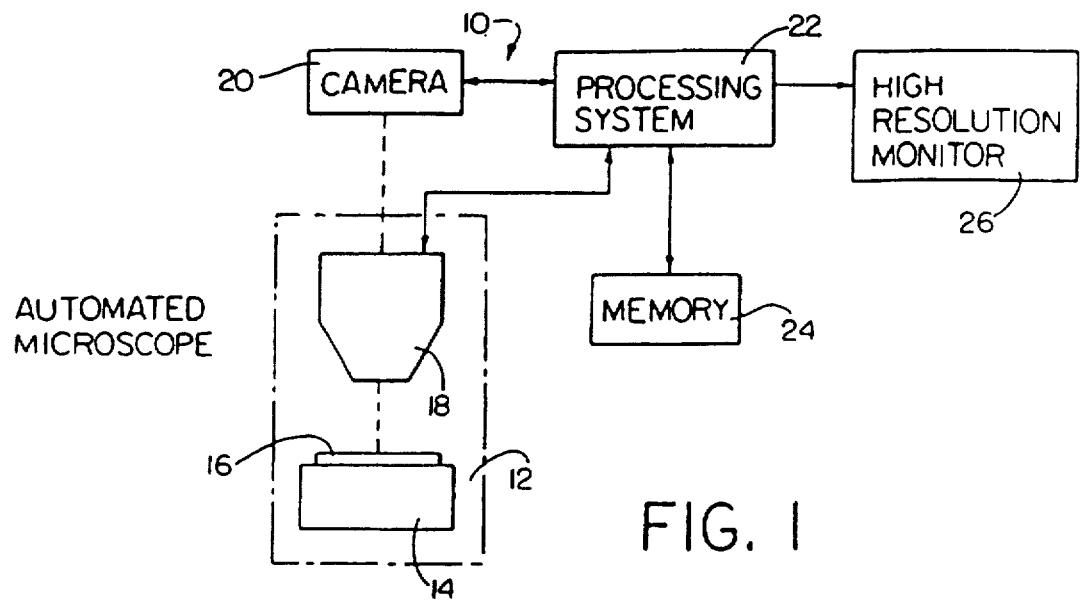
FIG. 1 is a schematic illustration of a histological classification or screening device in accordance with the present invention.

With reference to the several figures in which like reference numerals depict like items, and initially to FIG. 1, there is shown a semi-automated cell classification device 10 in accordance with the present invention. Briefly, the device 10 includes an automated optical microscope 12 having a motorized stage 14 for the movement of a slide 16 relative to the viewing region of the viewing portion 18 of the microscope, a camera 20 for obtaining electronic images from the optical microscope, a processing system 22 for classifying objects in the images as likely to be of a predetermined type, and a memory 24 and a high resolution color monitor 26 for the storage and display respectively of objects identified by the processing system as being likely to be of that predetermined type.

In its preferred embodiment the classification device 10 is semi-automated. In other words, the processing system 22 performs a classification of cells and cell clusters in a histological specimen and ranks the cells and clusters in an order according to the likelihood that each cell and cell cluster is, for example, a premalignant or premalignant cell or cell cluster. The cells and cell clusters which are ranked as most likely to be a premalignant or malignant cell or cell cluster are displayed on the monitor 26 for review by a skilled technician who can then make a final determination regarding whether each displayed cell and cell cluster is premalignant, malignant or otherwise indicative that further medical attention to the patient from whom the specimen was obtained is justified. Preferably the display of cells classified as likely to be malignant, for example, is separate from the display of cell clusters classified as likely to be malignant, such as by presenting the groups of cells or cell clusters one after another on the same monitor 26.

In view of the semi-automated nature of the classification device 10, the microscope 12 will preferably include, in addition to the motorized stage 14, automated apparatus for focussing, for changing lens objectives between high and low power, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, a cell dotter for marking relevant areas of the slide, and a bar code reader for reading encoded information from the slide. An example of a microscope performing at least some of these functions is manufactured by Carl Zeiss, Inc. of Germany, and a suitable motorized stage is manufactured by Ludl Electric Products, Ltd. of Hawthorne, N.Y.

Figure 2:
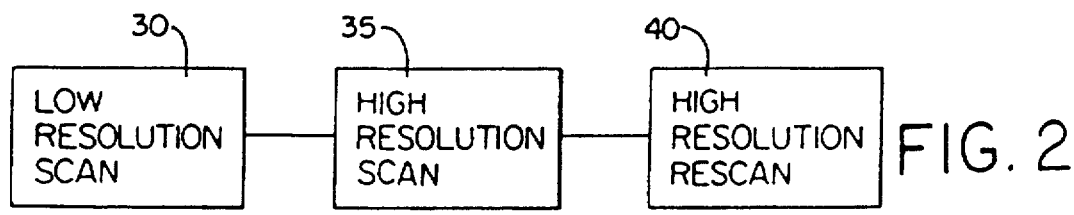
FIG. 2 is a diagrammatic illustration of the scanning passes which the screening device performs.

In accordance with the invention the automated microscope 12 preferably performs three scans of the slide having the specimen disposed thereon, as shown diagrammatically in FIG. 2. The first scan of the slide is performed at a relatively low magnification, for example 50 power, and is called the low resolution scan (30). The second scan is performed at a higher magnification, for example 200 power, and is called the high resolution scan (35). The third scan is referred to as the high resolution rescan and is also performed at a high magnification (40).

During the first scan (30) of the slide, approximate focal planes for the specific areas of the slide are found and it is determined whether that area of the slide contains a portion of the specimen. Once a low resolution scan (30) has been performed of the whole slide, and the focal planes and areas of the slide containing the specimen have been logged, the high resolution scan (35) is performed.

The high resolution scan (35) is performed only on the areas of the slide found in the low resolution scan (30) to contain a portion of the specimen. Consequently, the comparatively long high resolution scan (35) is performed only on relevant areas of the slide and the processing time is greatly reduced. During the high resolution scan (35), the automated microscope 12 scans the relevant areas of the slide, and the camera 20 takes electronic images of these areas and sends the images to the processing system 22. The processing system 22 performs a primary classification of the image which finds the centroids of biological objects having attributes typical of the cell class for which screening is being performed, such as malignant cells. Using a smaller sub-image centered around these centroids, the processing system 22 performs a secondary classification which assigns each centroid a value indicative of the possibility that the object having that centroid is a cell of the type for which classification is being performed. Simultaneously, the centroids are also ranked based on the value assigned through the secondary classification.

Upon completion of the high resolution scan (35), the high resolution rescan (40) is performed for, preferably, the highest ranked sixty-four cells and highest ranked sixty-four cell clusters, although other numbers of cells and cell clusters may be selected. During the rescan (40) the automated microscope 12 will move to each of the highest ranked centroids of the cells and cell clusters and the camera 20 will obtain a high resolution color image of the object having that centroid as well as the contextual surrounding matter. These high resolution images are then stored in the memory 24 which may be a removable device, such as an optical disk or a tape, etc., or a fixed storage device such as a hard disk. Alternatively, the images may be transferred to another computer via a network or through transportation of the data on a removable storage media.

The sixty-four cell images and sixty-four cell clusters make up two separate summary screens, one for the cell images and one for the cell clusters. Each summary screen is preferably arranged as an 8×8 matrix of high resolution color images, or tiles, featuring a suspect cell or cell cluster in the center of each image. It will be appreciated, however, that other numbers of images may be displayed concurrently to produce a summary screen, such as a 4×4 matrix. These summary screens are displayed on the high resolution color monitor 26 for tertiary analysis and classification, for example, by a technician. This analysis may take place at anytime after the classification process by the processing system 22 has been completed. Further, through the use of a removable memory device or a network connection, the images of the summary screens may be transferred to a workstation remote from the microscope 18, camera 20 and processing system 22 for display and analysis. In such an instance a separate graphics processor 41 may be employed to drive the high resolution color monitor 26 and provide a suitable interface with the technician.

Herein the screening method and apparatus of the present invention will be described as used in screening a conventionally prepared histological specimen slice as may be obtained from a tumor, such as a brain tumor, breast cancer tumor, a melanoma, or soft tissue sarcoma, to name a few examples, for the presence of malignant cells as opposed to benign tumor cells. However, it will be apparent to a person of ordinary skill in the art that this is only an illustrative use and that the present invention may be used in screening samples of other biological matter taken by a variety of histological or cytological sampling techniques, including cell blocking techniques. Further it will be apparent that while the illustrative example screens for malignant or premalignant cells, the screening may be performed for the detection of other cell classes of for detectible activity in a cell such as mitosis.

Figure 3:
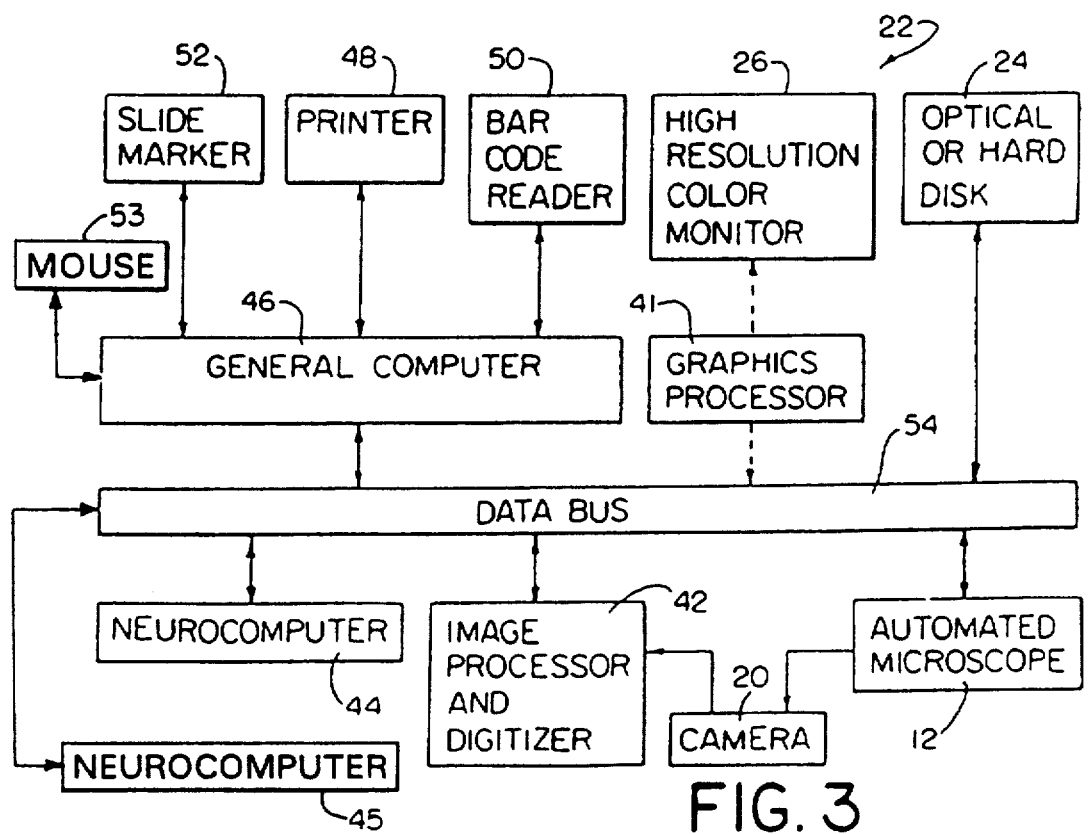
FIG. 3 is a schematic illustration of the screening device of FIG. 1 with particular emphasis on the processing system.

Turning now to a more in-depth discussion of the present invention with specific reference to FIG. 3, the screening device 10 is shown with particular emphasis on the classification elements embodied in the processing system 22. The processing system 22 preferably includes an image processor and digitizer 42, neurocomputers 44 and 45, and a general processor 46 with peripherals for printing, storage, etc.

The general processor 46 is preferably an Intel® 80486 microprocessor or similar microprocessor based microcomputer although it may be another computer-type device suitable for efficient execution of the functions described herein. The general processor 46 controls the functioning of and the flow of data between components of the device 10, may cause execution of additional primary feature extraction algorithms and handles the storage of image and classification information. The general processor 46 additionally controls peripheral devices such as a printer 48, a storage device 24 such as an optical or magnetic hard disk, a tape drive, etc., as well as other devices such as a bar code reader 50, a slide marker 52, autofocus circuitry, a robotic slide handler, the stage 14, and a mouse 53.

The image processor and digitizer 42 digitizes images from the video camera 20 and performs a primary algorithmic classification on the images to filter out unwanted information. The image processor and digitizer 42 (hereinafter collectively referred to as the image processor) performs two separate filtering operations. In one operation, the images of the specimen taken through the microscope 12 by the video camera 20 are filtered to find images representative of individual cells which have attributes of a premalignant or malignant cell. In a separate operation, which is preferably performed simultaneously with the first filtering operation, cell clusters having attributes of premalignant or malignant cell clusters are found.

Secondary cell classification is performed by the neurocomputers 44 and 45. Each neurocomputer is trained to handle the specific types of images provided by one of the filtering operations of the image processor 42. For example, the neurocomputer 44 is trained to recognize individual premalignant and malignant cells among the output of one of the filtering operations of the image processor 42, while the neurocomputer 45 is trained to recognize premalignant and malignant cell clusters or architectures among the images output by the other filtering operation. Alternatively, secondary cell classification functions could be performed using a single neurocomputer, or template matching algorithm designed to identify shapes known to be typical of a pathological cell or cell cluster. A template matching or other group processing algorithm could be efficiently implemented in a parallel distributed processing network, for example. Another alternative secondary classification embodiment is a holographic image processor designed to perform group based classification.

The image processor 42, the neurocomputers 44 and 45, and the general computer 46 may each access read-only and/or random access memory, as would be readily apparent to one skilled in the art, for the storage and execution of software necessary to perform the functions described relative to that processing component. Further, each component 42, 44, 45, 46 includes circuitry, integrated circuit chips, etc. for the control of communication or data transfer over the data bus 54 as well as other functions typical of similar processors as would be appreciated.

Figure 4:
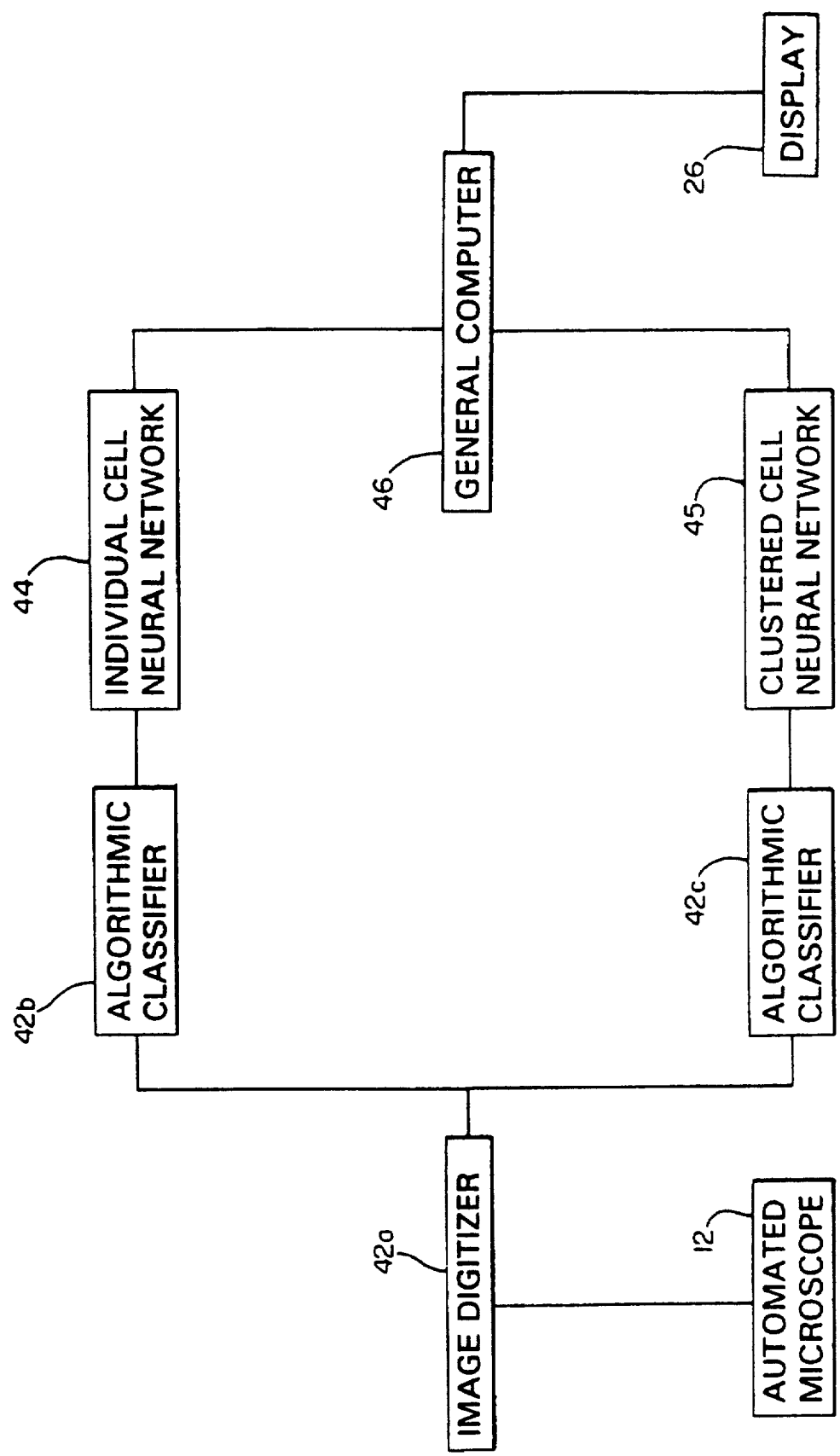
FIG. 4 is a flow diagram schematically illustrating the flow of image data through the classification device.

Referring to FIG. 4, there is shown a data flow diagram for the processing system 22. As shown, the image digitizer and image processor 42 is divided into three functional elements, 42a, 42b and 42c, to best represent the functional flow of image data through the image processor 42. When the automated microscope 12 focusses on an image in the specimen being analyzed during the high resolution scan (35), the image is presented to the image digitizer 42a which converts the image into a digital format. The digital image data is then subjected to two separate classification processes 42b and 42c designed to perform different filtering operations on the image data. The algorithmic classification functions 42b and 42c perform the primary classification.

The algorithmic classifier 42b is analogous to a band-pass filter which allows individual cells having morphological attributes consistent with a premalignant or malignant cell to pass through the classifier 42b. The classifier 42b filters out other objects and fragments, including cells which are too small to be a malignant cell, cells which are too large, cell clusters, and cells which have other features distinguishing them from malignant cells, for example red blood cells which are distinguishable by their intensity or brightness in the representative image. One embodiment of a suitable morphological algorithm is described in U.S. Pat. No. 5,257,182 which is incorporated by this reference. Many types of malignant cells tend to be dissociative and thus the algorithmic classifier 42b is optimized to find these dissociative cells which have the appropriate morphological characteristics of a premalignant or malignant cell and to pass those cells on to the neurocomputer 44 for further classification.

The algorithmic classifier 42c is analogous to a band-pass filter which passes cell groups or clusters and rejects individual, or dissociated, objects and cells. Many types of cancers found in histological specimens express themselves in certain architectures or clusters, while other cell clusters may have other diagnostic significance to a reviewer. The algorithmic classifier 42c is optimized to pass images of significant cell clusters to the neurocomputer 45 for further classification.

Preferably the algorithmic classifiers 42b and 42c, as well as the image digitization function 42a, are combined in a single processor 42 which permits both sequential and simultaneous processes. In the preferred embodiment, the image processor and digitizer 42 is a low level morphological feature extraction image classifier which includes among other things an image digitization function and an ISMAP (Iconic to Symbolic Mapping) board. A suitable image processor is described more fully in U.S. Pat. No. 4,601,055, the entire disclosure of which is incorporated by this reference. Alternatively, the image processing and digitization functions could be separated into two or more components.

The secondary classification is performed by the neurocomputers 44 and 45. Each neurocomputer 44, 45 is trained to recognize cells or cell clusters, depending upon its training, which are most likely to represent premalignant or malignant cells or cell clusters. The neurocomputer 44 and 45 are provided image data from the algorithmic classifiers 42b, 42c, respectively, which is consistent with its training. For example, the neurocomputer 44 is trained to recognize individual premalignant or malignant cells and is provided with image data which the algorithmic classifier has identified as having the morphological attributes of individual premalignant or malignant cells. Similarly, the neurocomputer 45 is trained to recognize premalignant or malignant cell clusters or architectures and is provided with image data which the algorithmic classifier 42c has identified as having the morphological attributes of premalignant or malignant cell clusters or architectures.

As noted above, the neurocomputer 44 is provided with image data from the primary algorithmic classifier 42b which consists of images of cells and other objects which the algorithmic classifier has identified as having attributes consistent with dissociated premalignant and malignant cells. In accordance with its training, the neurocomputer 44 assigns images in the data which are likely to represent premalignant or malignant cells with a relatively high value and assigns images that to the neural network are less likely to represent malignant cells, for example benign cells, with a lesser value. The sixty-four highest ranked cell images, i.e., those cell images most likely to represent premalignant or malignant cells are provided to the general computer 46.

The neurocomputer 45 is provided with image data representing cell clusters identified by the primary algorithmic classifier 42c. The neurocomputer 45, in accordance with its training, assigns images in the data which are likely to represent premalignant and malignant cell clusters with a relatively high value while assigning images which are likely to be benign with a lesser value. This time, the highest ranked sixty-four images of cell clusters are provided to the general computer 46.

The neural networks 44 and 45 are each preferably a computer embodiment of a neural network trained to identify suspect cells or cell clusters. In this embodiment the parallel structure of a two or three-layer backpropagation neural network is emulated with pipelined serial processing techniques executed on any of a number of commercially available neurocomputer accelerator boards. The operation of these neurocomputers, for example, is discussed in Hecht-Nielsen, Robert, "Neurocomputing: Picking the Human Brain", IEEE Spectrum, March, 1988, pp. 36–41. The neural networks are preferably implemented on an Anza Plus™ processor, which is a commercially available neurocomputer of Hecht-Nielsen Neurocomputers. Such a neurocomputer could be easily configured to operate in a manner suitable to perform the secondary classification functions by one of ordinary skill in the art through reference to corresponding manuals, etc.

Preferably each neurocomputer 44, 45 is trained with images of cells and cell clusters from histological specimens which have been classified by the corresponding primary algorithmic classifier and then reviewed by a person skilled in analyzing histological specimens for the presence of malignant cells and cell clusters. Such a person can readily review the cells and cell clusters which have been classified by the primary algorithmic classifiers 42b and 42c and determine whether the cells or cell clusters are benign or malignant. Operating in a training mode, the neurocomputer 44 is trained with images of individual objects classified as having morphological attributes of a malignant cell by the algorithmic classifier 42b which a skilled technician has determined to be malignant or benign. The images are fed through the neurocomputer and the neurocomputer is informed by the reviewer of the correct classification of the image as benign or malignant. Based on a series of such inputs the neurocomputer can organize itself to associate a known benign image with an output of 0.1 and a known malignant image with an output of 0.9. Such outputs represent, for example, the degree of certainty that a cell is normal or abnormal, respectively. When the secondary classifier is presented with new, unknown cells, it generalizes from its training and attaches a net value to the image. The closer that the secondary classifier is able to categorize the unknown image into the benign category, the closer is its net value equal to 0.1. Conversely, the more closely that the unknown image appears to resemble the nonbenign images of its training set, the closer is the net value assigned to that image equal to 0.9.

The neural network 45 is trained in the same way but with images of cell clusters which the primary algorithmic classifier 42c has identified as having morphological characteristics of premalignant or malignant cell clusters. The training may be tailored to certain cell architectures typically found in predetermined malignancies, such as melanomas, sarcomas, breast or brain tumors for example. These images are further classified by a skilled person who then assigns the images a value between 0.1 and 0.9 depending on whether the cell cluster is benign or malignant, and the neural network is provided with the known images and their respective values assigned by the skilled reviewer. A neurocomputer is effective at recognizing cell architectures which are complex as well as those which are presented in various orientations and configurations due to the method of obtaining the histological specimen.

The neurocomputers 44 and 45 may in some cases be trained based on other training sets while still being effective. For instance, it has been found that neurocomputers 44 and 45 trained with cytological images, such as from a Pap smear, that have been screened by the primary algorithmic classifiers 42b and 42c are still effective in finding malignant cells and cell clusters in certain histological specimens.

High resolution images of the cells and cell clusters ranked by the neurocomputers 44 and 45 as most likely to be representative of malignant cells or cell clusters are obtained through a rescan (40) of the automated microscope of the relevant areas on the specimen. The general computer 46 then stores the image in the memory 24, which may include an optical disk or tape, and makes the images available for viewing on the monitor 26 in separate summary screens or pages of information or for some other use. As discussed above, the first summary screen is preferably a display of the sixty-four cells classified by the neurocomputer 44 as most likely to be malignant cells. These cells and surrounding material on the slide, called tiles, are displayed in an arrangement, such as an eight by eight matrix, which facilitates review by a technician. A technician can easily visually scan this summary screen in search of images of cells having the attributes for which classification is being performed. If the system is being used to screen a tumor specimen to determine if the tumor is benign or cancerous, the technician would typically examine visually the first screen for cells having attributes of a malignant or premalignant cell, such as a comparatively large, dark nucleus. The technician is preferably permitted to interact with the general computer 46 through a mouse 53 to identify certain cells as malignant, to make other determinations or to cause the general computer to execute other commands or display different material.

The second screen, which includes images of cell clusters, often displays malignancies which are found as groups of cells or cell nuclei. However, other material on the second summary screen may also be of relevance to the technician in forming a diagnosis of the specimen. Manipulation of the screen display as well as interaction with the general computer 46 is again permitted through use of a mouse 53 or other interactive devices including a keyboard.

A histological specimen is generally taken from a tissue sample obtained during a tumor biopsy or during surgical removal of a tumor, although a histologic specimen may be taken of other tissues. To obtain a suitable histological specimen, a tissue sample is fixated or preserved by dehydration. The sample is then thinly sliced, such as with a scalpel, and placed within a chamber in a plastic cassette holder which is in turn placed in a conventional histological specimen processor. The specimen processor fills the chamber containing the dehydrated tissue slice with hot wax, such as paraffin wax, thus embedding the tissue slice within the paraffin. Once the embedded specimen has cooled, the specimen processor slices the specimen into one or more very thin slices, for example, slices less than 10 microns in thickness. One or more of these thin slices are then placed on a slide, side by side when more than one slice is to be inspected. The specimen slices on the slide are then stained to make certain features of the specimen visually distinguishable. A conventional group of stains are Hematoxylin and Eosin which, respectively, stain cell nuclei blue and cytoplasm and other material red. As a result of such a method of obtaining the histological specimen, clinically significant cell architectures and clusters may be found represented in many different orientations due to the location and angle of the slice taken in the initial tumor specimen.

The neurocomputers can effectively generalize a classification of these diverse representations from the known images presented during the training.

Other stains, such as immunolabeling stains, are specific to certain activity or occurrences within a cell and can detect, for example, cell mitosis or division. One such stain is MiB-1 which is a monoclonal antibody to certain antigens expressed in a nucleus of a cell around the time of mitosis. Consequently, the MiB-1 stain can be used to provide a visual indication of cell proliferation. As it is known that malignant cells tend to proliferate at a much faster rate than benign cells, an indication of a region in a specimen undergoing significant proliferation can provide important diagnostic information to the person reviewing the sample. This is especially true in multicellular fragments or clusters where the occurrence of proliferation is high.

The MiB-1 stain effectively dyes the nucleus of a cell brown while not significantly coloring the cytoplasm. In the instance of a histological tumor specimen, the MiB-1 stain is useful in providing diagnostic information on the specimen by itself or in conjunction with conventional Hematoxylin and Eosin staining. When used in connection with a conventional staining, the stained specimen can be destained using known techniques and then restained with the MiB-1 stain in a procedure such as that described below. Alternatively, since more than one specimen slice can be placed on a slide, it is possible to stain different slices on the same slide with different stains or immunochemicals. When it is not necessary that the specimen be first screened with a certain stain or when a different type specimen is used for which screening with a conventional stain is not desired, the MiB-1 stain may be applied to the specimen following a procedure such as that below without first destaining the specimen.

A suitable procedure for applying the MiB-1 stain to a previously unstained or destained specimen includes retrieving the antigens in the specimen such as by:

1) placing the specimen in plastic jar containing 10 mM citrate buffer, pH 6.0;
2) placing the plastic jar containing the specimen and citrate buffer in a microwave oven;
3) microwave heating the specimen to 100 degrees Celsius and maintaining the specimen at 100 degree Celsius for approximately 20 minutes;
4) cooling the specimen in the citrate buffer below a maximum temperature of 50 degrees Celsius; and
5) rinsing the specimen in TBS for approximately 2 minutes.

Once the antigen retrieval procedure is completed, the specimen is stained with the MiB-1 stain such as through the standard SAB protocol using an antisera dilution of 1:200 and counter staining with Hematoxylon. The standard SAB protocol is discussed in detail in Kok & Boon, "Microwave Cookbook for Microscopists: Art and Science of Visualization," Third edition, Coulomb Press Leyden, Leiden (1992).

Subjecting a MiB-1 stained specimen to the classification device 10 described above will result in the system producing two summary screen of objects for review by a technician. The first summary screen again contains images of individual objects and their contextual surrounding matter that the classification system ranked as most likely to represent premalignant or malignant cells. The second screen contains cell clusters ranked as most likely to represent premalignant or malignant cell clusters. As a result of the MiB-1 staining, and the selectivity of the stain to proliferating cell nuclei, the summary screens will contain individual premalignant and malignant cells and cell clusters undergoing mitosis as well as a number of benign cells that are proliferating, for example, Herpes Virocytes and cells from tissue repair. A technician can readily distinguish by visual inspection of the summary screens the premalignant and malignant cells and cell clusters from the benign ones.

Consequently, the classification device 10 used in conjunction with an immunochemical stain, finds the clinically most interesting proliferating cells for display and review by the technician. Since also cells may be stained which are benign the classification system is an effective means of isolating those cells or cell architectures in the specimen which are most relevant to a diagnosis of the histological specimen by a technician.

The technician can use the mouse 53 to select cells or cell clusters from the display 20 for grouping on the summary screen with other cells or clusters, to delete cells or clusters from the display as well as to command the general computer 46 to perform certain processing or calculations on the information in the summary screen. For example, a count of the number of proliferating cells in a specimen is a diagnostically significant measurement. The technician can review the summary screens, edit the display to remove certain objects or to designate others for counting, and then instruct the general processor 46, such as through use of the mouse 53 or a keyboard, to count the number of proliferating cells in the display. The technician can also mark cells in a tile of the summary screen, for example individual cells in a cell cluster, as positive staining or negative staining and instruct the general computer 46 to determine the percentage of positive staining nuclei in a tile or fragment. The classification can also be tailored to provide a total count of the brown stained cells in the specimens and in conjunction with the neurocomputers and/or the cytotechnician, a relative count of unstained to stained malignant cells in epithelial compartments.

Another diagnostically significant measurement is the area of the display that is stained. This is particularly relevant for cell clusters which are displayed on the second summary screen. Again, using the mouse 53 for example, the technician can review the images on the second screen, edit the screen by removing images, selecting images to form a separate screen of for example 16 significant images, and command the general computer 46 to determine the area of the display that is stained by the MiB-1 stain. The general processor 46 then calculates the stained area, such as a percentage of the total screen area, using conventional algorithmic techniques, and provides the result to the technician.

Through the interaction of the technician with the general processor 46 through use of a mouse 53 or similar interactive tool, and the ability to edit the images on the screen and identify characteristics of cells in the display or within individual tiles in the display, the technician can instruct the system to provide a large amount of diagnostic information which is specifically tailored to the specimen reviewed and the cellular material found in the specimen.

While the example given here of an immunolabeling dye is MiB-1 other types of immunochemical markers can be used in equivalent ways to indicate the desired characteristics in the specimen, such as proliferation or other characteristics. One supplier of immunochemical labels is ICN Biochemicals although many other suppliers are available. Further, the classification performed by the image processor 42 and neurocomputers 44 and 45 can be tailored to select images for display based on the detection of a feature made detectible by the immunochemical marker.

STATEMENT OF INDUSTRIAL APPLICATION

The present invention is applicable to cell classification in general and is particularly applicable to the classification of cells in a histological specimen.

What is claimed is:

1. A semi-automated method of classifying a specimen for the presence of premalignant or malignant cells, comprising the steps of:
   a) treating a specimen with an immunochemical marker to provide a visual indication of cell proliferation;
   b) ranking individual objects in the specimen in an order according to the likelihood that each object has attributes consistent with a premalignant or malignant cell or cell cluster;
   c) selecting for display a set of said objects according to said ranking; and
   d) displaying images of said selected objects to facilitate review by an operator.

2. The method of claim 1, wherein said individual objects include single cells.

3. The method of claim 1, wherein said individual objects include cell clusters.

4. The method of claim 1, wherein selected objects which represent individual cells are displayed separating from selected objects which represent cell clusters.

5. The method of claim 1, further including permitting the operator to edit the display to designate cells within the images of selected objects as proliferating or non-proliferating.

6. The method of claim 1, including the step of counting proliferation cells in said display.

7. The method of claim 5, including the step of counting cells designated by the operator as proliferating.

8. The method of claim 1, wherein said immunochemical marker is MiB-1 stain.

9. The method of claim 1, wherein said immunochemical marker stains the nuclei of proliferating cells.

10. The method of claim 9, including the step of calculating the area of said stained nuclei.

11. A semi-automated method of classifying a specimen, comprising the steps of:
   a) obtaining a specimen;
   b) classifying such specimen to determine the likelihood that individual objects in such specimen have attributes justifying further medical consideration, said classifying including
   ranking individual objects in the specimen in an order according to the likelihood that each object has attributes justifying further medical consideration, and
   selecting for display a plurality of such objects according to said order, said plurality of selected objects being less than the number of ranked objects; and
   c) displaying an image of each of said selected objects for review and further classification by an operator.

12. The method of claim 11, wherein said individual objects include cell clusters.

13. The method of claim 11, wherein selected objects which represent individual cells are displayed separating from selected objects which represent cell clusters.

14. The method of claim 11, further including the step of staining such specimen with an immunochemical marker.

15. The method of claim 1, wherein said specimen is a histological specimen.

16. The method of claim 1, wherein said specimen is a cytological specimen.

17. The method of claim 11, wherein said specimen is a histological specimen.

18. The method of claim 11, wherein said specimen is a cytological specimen.

19. The method of claim 1, wherein said selecting comprises selecting at least a minimum number of highest ranked objects regardless of whether the ranking of an object is greater than or less than a prescribed likelihood.

20. The method of claim 11, wherein said attributes include attributes of a premalignant or a malignant cell.

21. The method of claim 20, wherein said selecting comprises selecting at least a minimum number of highest ranked objects regardless of whether the ranking of an object is greater than or less than a prescribed likelihood.

22. The method of claim 1, wherein said displaying includes displaying said selected objects in an arrangement without regard to the ranking of each object.

23. The method of claim 11, wherein said displaying includes displaying said selected objects in an arrangement without regard to the ranking of each object.

* * * * *

UNITED STATES PATENT AND TRADEMARK OFFICE
CERTIFICATE OF CORRECTION

PATENT NO.: 5,544,650

DATED: August 13, 1996

INVENTOR(S): Mark R. Rutenberg, et al.

It is certified that error appears in the above-identified patent and that said Letters Patent is hereby corrected as shown below:

Claims 1 through 10, 14 through 17, 19, and 22 are canceled.

Signed and Sealed this

Second Day of June, 1998

Attest:

BRUCE LEHMAN

*Attesting Officer*    Commissioner of Patents and Trademarks